(12) United States Patent
Field

(10) Patent No.: US 8,092,390 B2
(45) Date of Patent: Jan. 10, 2012

(54) MEDICO-SURGICAL DEVICES

(75) Inventor: Stephen James Field, Canterbury (GB)

(73) Assignee: Smiths Group PLC, London (GB)

( * ) Notice: Subject to any disclaimer, the term of this patent is extended or adjusted under 35 U.S.C. 154(b) by 1360 days.

(21) Appl. No.: 10/196,151

(22) Filed: Jul. 17, 2002

(65) Prior Publication Data

US 2003/0040756 A1 Feb. 27, 2003

(30) Foreign Application Priority Data

Aug. 24, 2001 (GB) .................................. 0120645.7

(51) Int. Cl.
*A61B 8/14* (2006.01)
(52) U.S. Cl. ....................................... 600/458; 606/108
(58) Field of Classification Search .................. 600/458, 600/461, 566, 567; 606/108
See application file for complete search history.

(56) References Cited

U.S. PATENT DOCUMENTS

| | | | |
|---|---|---|---|
| 3,605,750 A * | 9/1971 | Sheridan et al. .............. 600/435 |
| 4,386,628 A * | 6/1983 | Stanley .......................... 138/97 |
| 4,805,628 A | 2/1989 | Fry et al. |
| 4,869,259 A | 9/1989 | Elkins |
| 4,874,649 A * | 10/1989 | Daubenbuchel et al. .... 428/36.5 |
| 5,048,530 A * | 9/1991 | Hurwitz ......................... 600/461 |
| 5,081,997 A | 1/1992 | Bosley, Jr. et al. |
| 5,201,314 A | 4/1993 | Bosley, Jr. et al. |
| 5,211,627 A | 5/1993 | William |
| 5,259,837 A | 11/1993 | Van Wormer |
| 5,289,831 A * | 3/1994 | Bosley .......................... 128/899 |
| 5,327,891 A | 7/1994 | Rammler |
| 5,383,466 A | 1/1995 | Partika |
| 5,646,194 A * | 7/1997 | Kobayashi et al. ............. 521/79 |
| 5,820,554 A * | 10/1998 | Davis et al. .................... 600/431 |
| 5,921,933 A | 7/1999 | Sarkis et al. |
| 5,967,988 A | 10/1999 | Briscoe et al. |
| 6,018,676 A | 1/2000 | Davis et al. |
| 6,106,473 A | 8/2000 | Violante et al. |
| 6,306,094 B1 | 10/2001 | Joseph |
| 6,506,156 B1 * | 1/2003 | Jones et al. .................... 600/439 |
| 6,527,752 B1 * | 3/2003 | Bosley et al. .................. 604/264 |
| 6,577,904 B1 | 6/2003 | Zhang et al. |
| 6,610,016 B1 | 8/2003 | Violante et al. |
| 6,723,052 B2 | 4/2004 | Mills |
| 6,905,458 B2 | 6/2005 | Choay et al. |
| 7,014,610 B2 | 3/2006 | Koulik |
| 7,229,413 B2 | 6/2007 | Violante et al. |
| 7,235,052 B2 | 6/2007 | Kellar et al. |
| 2002/0177776 A1 | 11/2002 | Crawford Kellar et al. |
| 2003/0206864 A1 | 11/2003 | Mangin |
| 2003/0208101 A1 | 11/2003 | Cecchi |
| 2005/0074406 A1 | 4/2005 | Couvillon, Jr. et al. |

(Continued)

FOREIGN PATENT DOCUMENTS

DE 3936162 6/1991

(Continued)

*Primary Examiner* — Gary Jackson
*Assistant Examiner* — Michael Mendoza
(74) *Attorney, Agent, or Firm* — Louis Woo

(57) ABSTRACT

An embryo replacement catheter has a flexible extruded shaft of a transparent polyurethane with a bore extending along its length. Gas bubbles of a diameter in the range 5µ to 10µ are incorporated into the thickness of the wall of the shaft by adding gas during extrusion. The bubbles are selected to increase the visibility of the catheter under ultrasound imaging whilst still enabling material flowing along the catheter to be seen.

3 Claims, 1 Drawing Sheet

U.S. PATENT DOCUMENTS

| | | |
|---|---|---|
| 2005/0143656 A1 | 6/2005 | Burbank et al. |
| 2007/0167822 A1 | 7/2007 | Webler et al. |
| 2007/0179575 A1 | 8/2007 | Esch et al. |
| 2007/0255140 A1 | 11/2007 | Violante et al. |
| 2007/0265516 A1 | 11/2007 | Wang |
| 2008/0058702 A1 | 3/2008 | Arndt et al. |
| 2008/0154136 A1 | 6/2008 | Webler |

FOREIGN PATENT DOCUMENTS

| | | |
|---|---|---|
| DE | 4014998 | 11/1991 |
| EP | 0386936 | 9/1990 |
| EP | 0624342 | 11/1994 |
| SU | 1255450 | 9/1986 |
| WO | 95/23615 | 9/1995 |
| WO | WO 98/19713 | 5/1998 |

* cited by examiner

MEDICO-SURGICAL DEVICES

BACKGROUND OF THE INVENTION

This invention relates to medico-surgical devices.

The invention is more particularly concerned with medico-surgical devices, such as catheters, that are visible under ultrasound observation.

Ultrasound imaging equipment is increasingly being used during surgical procedures to monitor the location of a device within the body. The visibility of a device under ultrasound depends on various factors including the difference between the acoustic impedance of the material of the device and that of the surrounding medium, such as the patient tissue or body fluid within which the device is located. This difference is relatively low with plastic devices such as catheters and may make conventional catheters difficult to locate. Even devices of metal, such as needles, present problems of visibility under ultrasound observation because of the directional nature of the reflections. In some orientations a metal needle may be clearly visible but in other orientations it may be considerably less visible.

Attempts have been made to increase the visibility of medico-surgical devices under ultrasound observation in various ways. The surface of the device may be modified, such as by forming grooves or indentations in its surface. A reflective coating may be applied to the device, such as incorporating bubbles, as described in WO98/19713 and EP0624342. Alternatively, a metal marker may be secured to a plastics catheter.

BRIEF SUMMARY OF THE INVENTION

It is an object of the present invention to provide an alternative medico-surgical device.

According to one aspect of the present invention there is provided a medico-surgical device of a plastics material, the material including gas bubbles through the major part of the thickness of the material in at least a part of the device such as to increase the visibility of the device under ultrasound imaging.

The device is preferably tubular and the gas bubbles may be provided around the entire circumference of the device or may be provided in a region of the device occupying only a part of the circumference of the device, such as a strip extending along the length of the device. The outer surface of the device may be smooth and uninterrupted by gas bubbles, and the device may have an inner surface that is smooth and uninterrupted by gas bubbles. The bubbles may have a diameter in the range 1μ to 50μ and preferably have a diameter in the range 5μ to 10μ. The bubbles may be substantially spherical. The device may be extruded, the gas bubbles being formed by addition of gas during extrusion of the device. Alternatively, the gas bubbles may be formed by a chemical foaming agent or by the incorporation of hollow microspheres into the plastics material. The plastics material is preferably substantially transparent, the size and density of the bubbles being selected such as to enable material flowing along the device to be viewed by the eye. The plastics material may be polyurethane.

According to another aspect of the present invention there is provided an embryo replacement catheter comprising a flexible, hollow, extruded shaft of a substantially transparent plastics material, the shaft including gas bubbles through the thickness of its wall, the density and size of the bubbles being selected to increase visibility of the catheter under ultrasound imaging whilst enabling an embryo within the catheter to be viewed by the eye, and the bore of the catheter being smooth and uninterrupted by the gas bubbles.

According to a further aspect of the present invention there is provided a method of making a medico-surgical device comprising the steps of extruding a plastics material while incorporating a gas into the wall of the device such as to form gas bubbles through the major part of the thickness of the wall of the device sufficient to increase the visibility of the device under ultrasound observation.

According to a fourth aspect of the present invention there is provided a method of making a medico-surgical device comprising forming a wall of a plastics material containing a chemical foaming agent such as to form gas bubbles through the major part of the thickness of the wall of the device sufficient to increase the visibility of the device under ultrasound observation.

According to a fifth aspect of the present invention there is provided a method of making a medico-surgical device comprising forming a wall of a plastics material containing hollow microspheres such as to form gas bubbles through the major part of the thickness of the wall of the device sufficient to increase the visibility of the device under ultrasound observation.

According to a sixth aspect of the present invention there is provided a device made by a method according to the above further aspect of the present invention.

An embryo-transfer catheter and its method of manufacture, according to the present invention, will now be described, by way of example, with reference to the accompanying drawings.

DETAILED DESCRIPTION OF THE PREFERRED EMBODIMENTS

Figure 1:
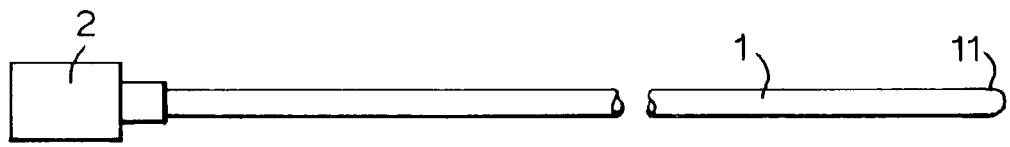
FIG. 1 is a side elevation view of the catheter.
Figure 2:
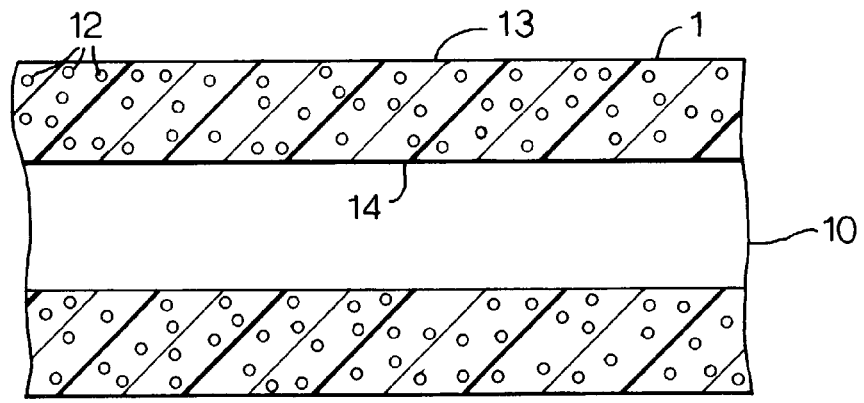
FIG. 2 is a sectional side elevation view of a part of the catheter of FIG. 1 to a larger scale.

With reference first to FIGS. 1 and 2, the catheter comprises a flexible shaft 1 and a hub 2 joined at the rear end of the shaft. The shaft 1 has a circular section and a bore 10 extending along its length. The shaft 1 opens at its forward, right-hand, patient end 11, which is atraumatically rounded. The shaft 1 is extruded from a clear, transparent polyurethane material and incorporates small, gas-filled bubbles 12 the size and distribution of which are selected to increase the visibility of the catheter under ultrasound observation. Typically, the gas bubbles have a diameter in the range of about 0.1μ to 300μ, preferably being between 1μ and 50μ with the most preferred range being 5μ to 10μ. As shown in FIG. 2, the gas bubbles are regions of gas bounded by the plastics material of the catheter forming an interface between the gas and the plastics material. The bubbles 12 extend through the entire thickness of the wall of the shaft 1 and may be spherical or of any other regular or irregular shape. The outer and inner surfaces 13 and 14 of the shaft may be smooth and uninterrupted by gas bubbles or the bubbles may break the surface.

The hub 2 serves to make connection with the shaft 1 and is moulded from a rigid, transparent plastics material, being subsequently bonded with the rear end of the shaft.

Figure 3:
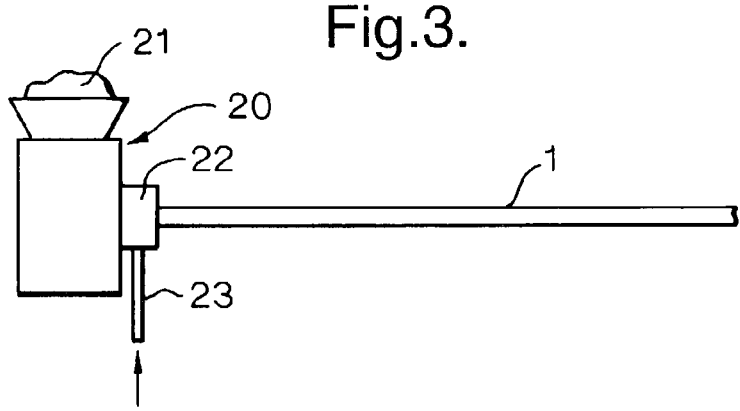
FIG. 3 illustrates schematically manufacture of the catheter.

The shaft 1 is extruded in the manner shown in FIG. 3 using an extrusion machine 20. Polyurethane material 21 is heated and supplied to the extrusion head 22 in the usual way but a gas such as nitrogen of carbon dioxide is also injected through the inlet 23 under pressure into the melt. As the plastics emerges from the extrusion head 22 the gas expands to form the bubbles 12. The relatively gas-permeable nature of the plastics means that after manufacture the bubble-forming gas will quickly escape and be replaced with air.

The shaft 1 can be extruded continuously at low cost, without the need for any subsequent operations apart from attaching the hub 2 and end forming the patient end tip 11.

The catheter shaft could be formed by other melt processes, such as injection moulding or blow moulding.

The bubbles could be formed in ways other than by injection of gas into the melt. For example, chemical foaming agents could be added to the plastics material, such as: azocarbonomides, dinitrosopentmethelyene-tetramine, benzenephonohydrazine, 4,4 oxybis(benzenephonohydrazine), $NN^1$dimethyl-$NN^1$ dinitrosoterephthalamide, azoisobutyronitrile, sodium bicarbonate, terephthalazide or trihydrazinatrazine. Another way of forming the gas bubbles would be by incorporating a liquid into the plastics melt which volatises during the melt process. Alternatively, solid powdered dry ice (carbon dioxide) could be incorporated into the melt so that the particles of dry ice become gas bubbles during the forming process. It might be possible to use other solids which undergo sublimation in this way. The bubbles could be formed directly as a result of chemical reaction during polymerisation and or alternatively during cross-linking. The bubbles could be formed mechanically by whipping the plastics in a liquid form, such as in the manner used to form latex foam. The bubbles could be formed by the incorporation of hollow microspheres of resin or glass. Alternatively, small particles of a soluble material could be added to the plastics melt and subsequently dissolved away.

A shaft of this kind can have good visibility under ultrasound imaging without producing multiple echoes and can produce a good image regardless of the orientation of the shaft. The shaft can be made sufficiently transparent to ultrasound energy to enable material flowing along the bore of the catheter to be observed on the ultrasound image.

Because the catheter does not require any coating or separate marker there is no need for subsequent assembly operations and there is no risk of detachment. The catheter can be made of conventional medically-approved materials so does not present any new risk to the patient. Because the surface of the catheter can be smooth, the catheter can be inserted or slid through an outer tube with low friction. The smooth bore of the catheter ensures free flow along the bore, which can be important where the catheter is used to transfer embryos. The smooth surfaces also reduce the accumulation of biofilm on the catheter. The catheter can be made without the need for metal components, which can be an advantage where the catheter is used while the patient is being viewed by magnetic imaging techniques. The catheter can be completely transparent to x-rays or the plastics from which it is formed could incorporate an x-ray opaque filler, such as barium sulphate.

The bubble size and density can be selected so that the optical transparency of the plastics forming the shaft remains sufficient to enable material flowing along the shaft to be viewed by the eye.

There are various ways in which the catheter could be modified. For example, it could be preferable for the bubbles to have a non-spherical shape and be oriented in a particular direction, such as longitudinally. This could be achieved by means of an obstruction in the extrusion die that constricts and elongates the bubbles as they flow through. Such an arrangement may give an increase in ultrasound visibility whilst reducing the opacity of the shaft to the eye.

Figure 4:
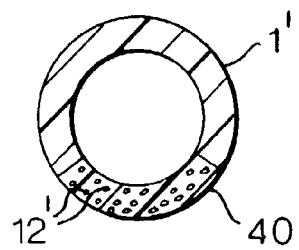
FIG. 4 is a sectional transverse view through an alternative catheter.

It is not essential for the bubbles to be provided around the entire circumference of the shaft. As shown in FIG. 4, the bubbles 12' could be formed only in one or more stripes extending along the shaft 1', such as in the stripe 40. This arrangement can be used where the shaft needs to have increased clarity so that material within the catheter can be seen by the eye. The bubble region need not be continuous along the length of the catheter. Instead, discrete separate regions with bubbles could be separated from one another along the length of the catheter by regions without bubbles. A shaft for such a catheter could be made by interrupting gas flow to the extruder. Where the bubbles are contained within a stripe, this could be interrupted to make it discontinuous by extruding the stripe using two auxiliary extruders, one having material with a blowing agent and the other having material without the blowing agent. Alternate extruders are switched on and off so that the stripe can have sections containing bubbles separated from one another by sections without bubbles. A catheter with an interrupted bubble region may give a clearer ultrasound indication of movement of the catheter along its length and may also enable clearer observation of material flowing along the catheter both by ultrasound and by the eye.

What I claim is:

1. A medico-surgical device of a plastics material, wherein said plastics material has a thickness, wherein said material includes gas bubbles through a major part of the thickness of said material in at least a part of the device, said gas bubbles in said material increasing the visibility of the device under ultrasound imaging, said gas bubbles being regions of gas bounded by the plastics material of the device forming an interface between the gas and the plastics material, wherein said region is a strip extending along the length of the device.

2. A method of making a medico-surgical device comprising the steps of: extruding a plastics material to form a wall having a thickness; and incorporating a gas into said wall during extrusion such as to form gas bubbles through a major part of the thickness of said wall sufficient to increase the visibility of said device under ultrasound observation, said gas bubbles being regions of gas bounded by the plastics material of the device forming an interface between the gas and the plastics material.

3. A method of making a medico-surgical device comprising forming a wall of a plastics material containing hollow microspheres such as to form gas bubbles through a major part of a thickness of the wall sufficient to increase the visibility of said device under ultrasound observation, said gas bubbles being regions of gas bounded by the plastics material of the device forming an interface between the gas and the plastics material.

* * * * *